(12) United States Patent
Delledonne et al.

(10) Patent No.: US 7,368,623 B2
(45) Date of Patent: May 6, 2008

(54) PROCESS FOR PRODUCING 1-OCTENE FROM BUTADIENE IN THE PRESENCE OF TITANIUM CATALYSTS

(75) Inventors: Daniele Delledonne, Oleggio-Novara (IT); Franco Rivetti, Milan (IT)

(73) Assignee: Polimeri Europa S.p.A., Brindsi (IT)

( * ) Notice: Subject to any disclaimer, the term of this patent is extended or adjusted under 35 U.S.C. 154(b) by 0 days.

(21) Appl. No.: 10/576,463

(22) PCT Filed: Oct. 11, 2004

(86) PCT No.: PCT/EP2004/011461

§ 371 (c)(1),
(2), (4) Date: Dec. 4, 2006

(87) PCT Pub. No.: WO2005/031045

PCT Pub. Date: Apr. 7, 2005

(65) Prior Publication Data

US 2007/0179327 A1    Aug. 2, 2007

(30) Foreign Application Priority Data

Oct. 27, 2003   (IT)  .......................... MI2003A2084

(51) Int. Cl.
*C07C 2/04*       (2006.01)
*C07C 5/05*       (2006.01)
(52) U.S. Cl. ....................... 585/329; 585/324; 585/273
(58) Field of Classification Search ................ 585/329, 585/324, 273
See application file for complete search history.

(56) References Cited

U.S. PATENT DOCUMENTS 4,229,605 A    10/1980  Nozaki
4,243,829 A    1/1981   Pittman et al.

FOREIGN PATENT DOCUMENTS

| EP | 0 008 139 | 2/1980 |
| EP | 0 704 417 | 4/1996 |
| WO | 03/031378 | 4/2003 |

OTHER PUBLICATIONS

Roffia, P. et al., "Catalysis by Palladium Salts", Journal of Organometallic Chemistry, vol. 55, pp. 405-407, 1973.
Sloan, Martin F. et al., "Soluble Catalysts for the Hydrogenation of Olefins", Journal of The American Chemical Society, vol. 85, No. 24, pp. 4014-4018, Dec. 1963.
U.S. Appl. No. 10/576,144, filed Apr. 18, 2006, Delldonne et al.

*Primary Examiner*—Thuan Dinh Dang
(74) *Attorney, Agent, or Firm*—Oblon, Spivak, McClelland, Maier & Neustadt, P.C.

(57) ABSTRACT

A method is described for the preparation of 1-octene starting from butadiene, wherein in a first step (a) the bis-hydrodimerization of butadiene to 1,7-octadiene is effected in the presence of a catalyst based on palladium containing one or more tri-substituted monodentate phosphines, in an aprotic polar solvent, in a second step (b) the partial catalytic hydrogenation of 1,7-octadiene to 1-octene is effected in the presence of a titanium compound activated with one or more metal alkyls of group 13 (selected from boron, aluminum, gallium, indium).

21 Claims, No Drawings

PROCESS FOR PRODUCING 1-OCTENE FROM BUTADIENE IN THE PRESENCE OF TITANIUM CATALYSTS

The present invention relates to a process for the preparation of 1-octene from butadiene in two steps, more specifically a first step for the catalytic bis-hydrodimerization of butadiene to 1,7-octadiene in the presence of a hydrogen donor, in an aprotic polar solvent, and a second step for the partial and selective reduction of 1,7-octadiene with hydrogen to 1-octene in the presence of a catalytic system comprising a titanium compound activated with an alkyl metal of group 13.

1-octene is widely applied in the field relating to the production of linear low density polyethylene (LLDPE), a copolymer obtained starting from ethylene and $C_4$-$C_8$ 1-olefins as comonomers, as it imparts improved mechanical characteristics and a better weldability to the end-product. It is also applied in the field of plasticizers after hydroformylation, reduction to linear alcohols and esterification.

The synthesis of 1-octene starting from butadiene is known in the state of the art.

Some patents describe the synthesis of 1-octene from butadiene by means of a three-step process. In U.S. Pat. No. 5,030,792, in a first step the catalytic telomerization of butadiene is effected with acetic acid to give 2,7-octadienyl acetate; the latter, in a second step, is hydrogenated to n-octyl acetate which, in turn, in a third step, is pyrolyzed to 1-octene. This type of process is jeopardized by the high number of reaction steps and is also characterized by corrosion problems of the common materials linked to the use of acetic acid.

WO 92/10450 describes the catalytic telomerization of butadiene with an alcohol such as methanol or ethanol to give 2,7-octadienyl ether. The latter, in a second step, is hydrogenated to octyl ether which, in turn, in a third step, is pyrolyzed to 1-octene. Although it avoids the use of corrosive carboxylic acids, this type of process is also jeopardized by the high number of reaction steps and an lower overall selectivity.

Finally, WO 03/31378 describes the synthesis of 1-octene in only two steps starting from butadiene according to the scheme of equations (1) and (2)

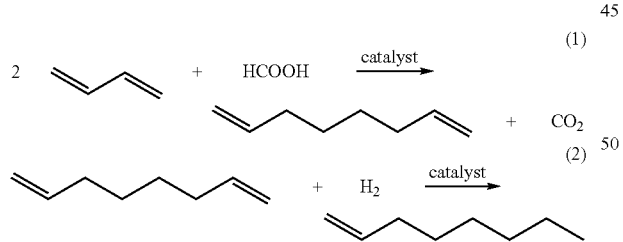

In the first step of the described process, the catalytic bis-hydrodimerization of butadiene to 1,7-octadiene is effected with a reducing agent such as formic acid. In the second step, the partial catalytic hydrogenation is carried out, of 1,7-octadiene to 1-octene.

Although the process described in WO 03/31378 has the advantage, with respect to the previous processes, of reducing to two, the number of steps necessary for producing 1-octene from butadiene, it has numerous drawbacks and in particular the necessity of using, both in the first and in the second step, high quantities of costly noble metals as catalysts.

The first step of the process of WO 03/31378 is carried out according to a reaction known in literature, i.e. the bis-hydrodimerization of butadiene in the presence of formic acid and catalysts based on palladium and phosphines. The reaction described is, in all cases, scarcely selective, with the formation of mixtures of 1,6-octadiene and 1,7-octadiene or 1,3,7-octatriene, and the yields and catalytic efficiency, moreover, are low.

Furthermore, it is necessary to use high quantities of catalyst, with molar ratios between the butadiene and palladium ranging from about 1000 to 2000, which create problems relating to the cost and recovery of the catalyst. If the concentration of catalyst is reduced to lower values, the selectivity to 1,7-octadiene decreases.

From what is specified above, it would appear necessary to avail of a more efficient process for the hydrodimerization of butadiene which allows high conversions and selectivities to 1,7-octadiene to be reached, also when operating with reduced concentrations of noble metal.

The second step of the process described in WO 03/31378 consists in the partial hydrogenation of 1,7-octadiene to 1-octene. The reaction, as described in WO 03/31378, i.e. carried out with a supported catalyst based on ruthenium in heterogeneous phase, suffers from an extremely low catalytic activity. Very long reaction times, in the order of over 24 hours, are in fact required for obtaining a conversion of 1,7-octadiene of 70% and a selectivity to 1-octene of 60%, and furthermore, it does not avoid the formation of isomer olefins. Also in this case, the quantity of catalyst used (or supported ruthenium) is much higher, due to the low catalytic activity of the catalyst adopted.

The necessity is therefore felt, also for this step, for a more efficient and more selective partial reduction of the 1,7-octadiene, even when operating with low quantities of catalyst.

A process has now been found for the preparation of 1-octene starting from butadiene, which overcomes the above drawbacks.

In accordance with this, the present invention relates to a process in two steps for the preparation of 1-octene starting from butadiene which comprises:

a first step (a) in which the bis-hydrodimerization of butadiene to 1,7-octadiene is effected in the presence of a catalyst based on palladium containing one or more tri-substituted monodentate phosphines, the molar ratio palladium/phosphines ranging from 50 to 3, more preferably from 30 to 5, in an aprotic polar solvent optionally containing an organic base; the above first step being carried out in the presence of a hydrogen donor, preferably formic acid, preferably in a stoichiometric ratio of 1:2 molar with respect to the butadiene;

a second step (b) in which the partial catalytic hydrogenation of 1,7-octadiene, recovered at the end of the first step, to 1-octene, is effected; the above hydrogenation being carried out under hydrogen pressure or mixtures of hydrogen and nitrogen, in the presence of a catalyst; the above process being characterized in that in step (b) the catalyst is selected from titanium compounds in the presence of activators selected from one or more metal alkyls of group 13 (i.e. selected from boron, aluminum, gallium, indium).

With respect to the first step (a), i.e. the bis-hydrodimerization of butadiene to 1,7-octadiene, the palladium-based catalyst is preferably selected from palladium carboxylates, even more preferably from palladium pivalate and Pd(acetate)$_2$. As far as the phosphine is concerned, typical examples are triphenyl phosphine, tri(o-tolyl)phosphine, (3-sulfonatephenyl) diphenyl phosphine, tricyclohexyl phosphine, trimethyl phosphine, triethyl phosphine, triisopropyl phosphine, tributyl phosphine, and mixed phosphines methyl diphenyl phosphine, dimethyl phenyl phosphine, singly or combined with each other. Triphenyl phosphine is preferred.

Again with respect to the first step, typical examples of aprotic polar solvents are disubstituted amides, for example dimethyl formamide, or disubstituted cyclic ureas, for example dimethyl ethylene urea or dimethyl propylene urea and the relative mixtures.

As far as the organic base is concerned, typical examples are pyridines, N-alkyl morpholines, trialkyl amines. In the preferred embodiment, the organic base is triethyl amine.

The first step is carried out in the presence of a hydrogen donor, preferably in a stoichiometric ratio of 1:2 molar with respect to the butadiene, see equation (1), or slightly lower. The hydrogen donor is preferably formic acid.

The butadiene is used in an initial weight ratio ranging from 1:10 to 10:1 with respect to the solvent, more preferably from 1:5 to 5:1.

The molar ratio between the organic base, for example triethyl amine and the hydrogen donor, for example formic acid, can vary from 0 to 1.5, more preferably from 0.2 to 1.3, and even more preferably from 0.4 to 0.8.

The reaction is carried out at temperatures ranging from 50 to 120° C., preferably from 70 to 100° C., preferably under a nitrogen pressure ranging from 0.5-2 MPa, more preferably from 0.8 to 1.5 MPa.

The duration of the reaction of step (a) indicatively ranges from 10 to 180 minutes, more preferably from 15 to 120 minutes.

According to the above process, in the first step, it is possible to improve the selectivity to 1,7-octadiene even in the presence of an extremely reduced quantity of catalyst, for example such that the initial molar ratio butadiene/palladium ranges from 5,000 to 1,000,000, preferably from 20,000 to 200,000, without significantly reducing the conversion of the butadiene, which is maintained high.

At the end of the first step, the reaction product 1,7-octadiene can be recovered according to the conventional techniques. More specifically, in a preferred embodiment of the invention, after the recovery of the butadiene, the reaction product is separated by demixing, exploiting the fact that 1,7-octadiene is not miscible in all ratios in the pre-selected solvent, for example dimethyl formamide, whereas the lower phase, comprising the solvent, optional organic base and catalyst, can be recycled to the reaction. The upper hydrocarbon phase, prevalently consisting of 1,7-octadiene, can be purified from the non-hydrocarbon residues by washing with water; the 1,7-octadiene is subsequently purified with conventional methods, for example by distillation.

According to an aspect of the invention, the carbon dioxide, co-produced in a stoichiometric quantity when formic acid is used as hydrogen donor, can be hydrogenated again to formic acid with hydrogen, to be then recycled to the reaction. The hydrogenation of carbon dioxide to formic acid is carried out, for example, as described in *Nature*, vol. 368, Mar. 17, 1994, page 231.

Operating according to the process object of the invention, the second step of the process, i.e. the partial catalytic hydrogenation of 1,7-octadiene to 1-octene, is carried out in the presence of a catalyst consisting of a titanium compound activated with one or more metal alkyls of group 13 (i.e. selected from boron, aluminum, gallium, indium).

The metal alkyl is preferably an aluminum alkyl.

Titanium compounds suitable for the purpose are tetra-alcoholates having the general formula $Ti(OR)_4$, wherein $R=CH_3$, $C_2H_5$, propyl, isopropyl, butyl, isobutyl, t-butyl, Ph or complexes having the general formula $(Cp)_nTiX_m$ wherein Cp=cyclopentadienyl, n+m=4, n=1 or 2, X=Cl, Br, $CH_2Ph$, $N(R)_2$, or OR, wherein R has the meaning defined above. More preferably, titanium compounds are selected from $Ti(OtBu)_4$, $Ti(EtO)_4$ and $Cp_2TiCl_2$.

Aluminum alkyls suitable for the purpose are aluminum trialkyls and alkyl alumoxanes, for example $Al(CH_3)_3$, (TMA), $Al(CH_2CH_3)_3$ (TEA), $Al(CH_2CH_2(CH_3)_2)_3$ (TIBA), $AlH(CH_2CH_2(CH_3)_2)_2$ (DIBAH) and methyl aluminoxane (MAO).

In a preferred embodiment, the hydrogenation reaction is carried out in a solution of hydrocarbon solvents. The hydrocarbon solvent is preferably selected from those in which the catalyst and relative activator are both soluble. As an example, solvents suitable for the hydrogenation are: $C_5$-$C_{14}$ aliphatic hydrocarbons, $C_5$-$C_{12}$ cyclo-aliphatic hydrocarbons, $C_6$-$C_{12}$ aromatic or alkyl aromatic hydrocarbons, or their mixtures.

When a solvent is used, the diene is contained in the solvent in a ratio of 5 to 90% by weight, more preferably from 10 to 80% by weight.

The catalyst is added to the reaction in a molar ratio with respect to the diene ranging from 1/100 to 1/100,000, preferably from 1/1,000 to 1/10,000, whereas the activator is used in a molar ratio with respect to the catalyst ranging from 1/1 to 10,000/1, more preferably from 1/1 to 2000/1.

The reaction is generally carried out at a temperature ranging from 0° C. to 150° C., preferably from 50° C. to 120° C. This range represents the field of temperatures in which the catalytic system has the minimum isomerization activity of the double bond compatible with a good reaction rate.

The reaction is generally carried out under hydrogen pressure or mixtures of hydrogen and nitrogen, preferably in the presence of hydrogen alone, at a pressure ranging from 0.05 to 10 MPa, preferably from 0.1 to 3 MPa.

The reaction time ranges from 1 to 400 minutes, more preferably from 5 to 120 minutes.

In order to limit the consecutive hydrogenation reaction of 1-octene to octane, the reaction is preferably carried out at a partial conversion of 1,7-octadiene lower than 80%, preferably ranging from 40 to 60%.

When the conversion value is within this range, selectivities to 1-octene are obtained, generally ranging from 75 to 90%. Furthermore, when operating according to the invention, the other isomers of 1-octene and 1,7-octadiene are normally absent, or in any case are formed with an overall selectivity generally lower than 2%.

The present invention is now described in detail by means of a few examples.

EXAMPLES

Synthesis of 1,7-octadiene

Examples 1 to 5

The following products are placed, in the order indicated and in the quantities specified in Table 1 or hereunder, in a Hastelloy C autoclave having a volume of 300 ml and equipped with a mechanical stirring system and heating system: 45 ml of dimethyl formamide (DMF) as solvent, 15 ml of triethyl amine, formic acid (concentration 99% by weight) in a stoichiometric quantity (0.5 moles/mole) with respect to the butadiene, $Pd(CH_3COO)_2$ as catalyst and triphenylphosphine as ligand. Finally, the autoclave is closed and 20 g of butadiene are added. The autoclave is pressurized with nitrogen at 0.1 MPa and the heating is initiated to a temperature of 90° C. for 90 minutes. At the end, the autoclave is cooled, the contents are treated with water and sodium bicarbonate and are extracted with cyclohexane. The products are quantified by gas chromatography with the internal standard method. The conversion of butadiene and selectivities referring to the butadiene converted are indicated in Table 1.

|  | Molar ratio $PPh_3/Pd$ | Molar ratio BD/Pd | Conversion % BD | Selectivity % 1,6-octadiene | Selectivity % 1,7-octadiene |
|---|---|---|---|---|---|
| Example 1 comparative | 2 | 2128 | 77 | 21 | 77 |
| Example 2 | 19 | 1627 | 82 | 9 | 89 |
| Example 3 comparative | 2 | 22457 | 46 | 17 | 83 |
| Example 4 | 10 | 22258 | 77 | 10 | 90 |
| Example 5 | 21 | 23526 | 61 | 10 | 89 |

Table 1 very clearly shows that the use of phosphine/Pd molar ratio values according to the invention has the effect of increasing the selectivity to 1,7-octadiene and also makes it possible to use an extremely reduced quantity of catalyst without significantly jeopardizing the butadiene conversion, which is maintained high.

With the same BD/Pd ratio, in fact, (comparative example 1 vs. example 2, and comparative example 3 vs. examples 4 and 5) the increase in the molar ratio $PPh_3/Pd$ allows a better yield and high selectivity to be obtained.

Hydrogenation of 1,7-octadiene to 1-octene

Examples 6 to 10

The following products are placed, in the order indicated and in the type and quantities specified in Table 2 or hereunder, in a glass flask having a volume of 250 ml, put under Argon: 100 ml of toluene as solvent, the quantity of 1,7-octadiene (1,7-OD) necessary for reaching the desired 1,7-OD/catalyst ratio, 0.03 mmoles of catalyst, the activator and finally the titanium catalyst, in order.

The products are left in contact for about 30 minutes in an inert atmosphere and the whole mixture is then transferred to a Hastelloy C autoclave having a volume of 300 ml, equipped with heat exchange devices and a mechanical stirring system, leaving a slight overpressure of argon. The autoclave is heated to the desired temperature (see Table 2), hydrogen is then introduced at a pressure of 2 MPa and the autoclave is connected to a make-up system of the hydrogen used up. A representative sample of the contents of the autoclave is taken at pre-fixed times and is subjected to gas chromatographic analysis, using the internal standard method, to determine the residual 1,7-octadiene, the 1-octene product, the 1-octane co-product and diene and monoene isomers. The selectivities refer to the 1,7-octadiene converted. The results are indicated in Table 2.

TABLE 2

| Example nr. | Catalyst/Activator | Molar ratios Catalyst/Activator | 1,7-OD/Catalyst | T °C. | t min | conv. % 1,7-OD | Sel. % 1-octene | Sel. % octane | Sel. % isomers |
|---|---|---|---|---|---|---|---|---|---|
| 6 | $(Cp)_2TiCl_2$/DIBAH | 1/24 | 2945 | 50 | 10 | 2% | 100% | 2% | 0% |
|  |  |  |  | 50 | 30 | 16% | 92% | 9% | 0% |
|  |  |  |  | 50 | 60 | 43% | 82% | 19% | 0% |
|  |  |  |  | 50 | 120 | 70% | 67% | 33% | 0% |
| 7 | $(Cp)_2TiCl_2$/MAO | 1/47 | 3290 | 50 | 10 | 35% | 85% | 15% | 0% |
|  |  |  |  | 50 | 30 | 60% | 75% | 26% | 0% |
|  |  |  |  | 50 | 60 | 79% | 59% | 41% | 0% |
| 8 | $(Cp)_2TiCl_2$/TIBA | 1/50 | 3470 | 53 | 5 | 20% | 98% | 10% | 0% |
|  |  |  |  | 51 | 15 | 37% | 88% | 16% | 0% |
|  |  |  |  | 50 | 35 | 54% | 79% | 24% | 0% |
|  |  |  |  | 50 | 95 | 67% | 70% | 32% | 0% |
| 9 | $Ti(tButO)_4$/TIBA | 1/14 | 3459 | 50 | 15 | 24% | 87% | 11% | 2% |
|  |  |  |  | 50 | 45 | 46% | 80% | 19% | 1% |
|  |  |  |  | 50 | 90 | 64% | 71% | 28% | 1% |
|  |  |  |  | 50 | 150 | 73% | 64% | 34% | 2% |
| 10 | $Ti(EtO)_4$/MAO | 1/100 | 3459 | 63 | 5 | 44% | 82% | 17% | 0% | tBut = $C(CH_3)_3$, Et = $C_2H_5$, Cp = cyclopentadienyl, TIBA = $Al•(CH_2CH(CH_3)_2)_3$, DIBAH = $AlH(CH_2CH(CH_3)_2)_2$, MAO = methyl aluminoxane Table 2 clearly shows that, when operating according to the invention, the partial reduction of 1,7-octediene to 1-octene takes place in the absence of or with extremely low isomerization levels.

The invention claimed is:

1. A process in two steps for the preparation of 1-octene starting from butadiene which comprises:
    a first step (a) in which the bis-hydrodimerization of butadiene to 1,7octadiene is effected in the presence of a catalyst based on palladium containing one or more tri-substituted monodentate phosphines, the molar ratio palladium/phosphines ranging from 50 to 3, in an aprotic polar solvent optionally containing an organic base; the above first step being carried out in the presence of a hydrogen donor;
    a second step (b) in which the partial catalytic hydrogenation of 1,7octadiene, recovered at the end of the first step, to 1-octene, is effected; the above hydrogenation being carried out under hydrogen pressure or mixtures of hydrogen and nitrogen, in the presence of a catalyst;
    the above process being characterized in that in step (b) the catalyst is selected from titanium compounds in the presence of activators selected from one or more metal alkyls of group 13.

2. The process according to claim 1, wherein in the first step, the molar ratio palladium/phosphine ranges from 30 to 5.

3. The process according to claim 1, wherein in the first step, the hydrogen donor is formic acid.

4. The process according to claim 1, wherein the hydrogen donor is in a stoichiometric ratio of 1:2 with respect to the butadiene.

5. The process according to claim 1, wherein the catalyst based on palladium is selected from palladium carboxylates.

6. The process according to claim 5, wherein the palladium carboxylate is $Pd(acetate)_2$.

7. The process according to claim 1, wherein in the first step, the aprotic polar solvent is selected from disubstituted amides and disubstituted cyclic ureas.

8. The process according to claim 7, wherein the disubstituted amide is dimethyl formamide.

9. The process according to claim 7, wherein the disubstituted cyclic ureas are selected from dimethyl ethylene urea and dimethyl propylene urea.

10. The process according to claim 1, wherein in the first step, the organic base is triethyl amine.

11. The process according to claim 1, wherein the temperature of the first step ranges from 50 to 120 20 C.

12. The process according to claim 11, wherein the temperature of the first step ranges from 70 to 100° C.

13. The process according to claim 1, wherein in the first step, the molar ratio between organic base and hydrogen donor ranges from 0 to 1.5.

14. The process according to claim 13, wherein the molar ratio between organic base and hydrogen donor ranges from 0.2 to 1.3.

15. The process according to claim 14, wherein the molar ratio between organic base and hydrogen donor ranges from 0.4 to 0.8.

16. The process according to claim 1, wherein the selective hydrogenation of 1,7-octadiene to 1octene is carried out in the second step in the presence of a catalytic system comprising one or more catalysts selected from titanium compounds and one or more activators selected from aluminum alkyls and aluminoxanes.

17. The process according to claim 16, wherein the molar ratio between the catalyst and 1,7-octadiene ranges from 1/100 to 1/100,000.

18. The process according to claim 16, wherein the molar ratio between the activator and catalyst ranges from 1/1 to 10,000/1.

19. The process according to claim 16, wherein the second step is carried out at a temperature ranging from 0° C. to 150° C.

20. The process according to claim 16, wherein the titanium compound is selected from the group consisting of $Ti(OtBut)_4$, $Ti(EtO)_4$ and $Cp_2TiCl_2$.

21. The process according to claim 16, wherein the activator is selected from the group consisting of MAO (methyl aluminoxane), TIBA (aluminum triisobutyl), DIBAH (diisobutyl aluminum hydride), TMA (trimethyl aluminum), TEA (triethyl aluminum).

* * * * *

UNITED STATES PATENT AND TRADEMARK OFFICE
CERTIFICATE OF CORRECTION

PATENT NO. : 7,368,623 B2
APPLICATION NO. : 10/576463
DATED : May 6, 2008
INVENTOR(S) : Delledonne et al.

It is certified that error appears in the above-identified patent and that said Letters Patent is hereby corrected as shown below:

On the title page, Item (87), the PCT Publication information is incorrect. Item (87) should read:

Item -- (87)  PCT Pub. No.: WO2005/047218
PCT Pub. Date: May 26, 2005 --

On the title page, Item (73), the Assignee information is incorrect. Item (73) should read:

Item -- (73)  Assignee: Polimeri Europa S.p.A., Brindisi (IT) --

Signed and Sealed this

Twenty-second Day of July, 2008

JON W. DUDAS
*Director of the United States Patent and Trademark Office*